United States Patent [19]

Schwalm

[11] Patent Number: 5,159,088

[45] Date of Patent: Oct. 27, 1992

[54] SULFONIUM SALTS AND USE THEREOF

[75] Inventor: Reinhold Schwalm, Wachenheim, Fed. Rep. of Germany

[73] Assignee: BASF Aktiengesellschaft, Ludwigshafen, Fed. Rep. of Germany

[21] Appl. No.: 551,779

[22] Filed: Jul. 12, 1990

[30] Foreign Application Priority Data

Jul. 22, 1989 [DE] Fed. Rep. of Germany ....... 3924298

[51] Int. Cl.$^5$ .......................... C07C 69/96; C07F 9/68
[52] U.S. Cl. .......................................... 549/3; 549/4; 549/9; 549/49; 549/77; 549/79; 549/80; 556/64; 558/271; 558/274
[58] Field of Search ................. 556/64; 568/6, 28, 75, 568/77; 549/3, 4, 6, 49, 77, 79, 80; 558/271, 274

[56] References Cited

U.S. PATENT DOCUMENTS

| | | |
|---|---|---|
| 2,807,648 | 9/1957 | Pitt . |
| 2,833,827 | 5/1958 | Hahn et al. . |
| 4,058,400 | 11/1977 | Crivello . |
| 4,058,401 | 11/1977 | Crivello . |
| 4,491,628 | 1/1985 | Ito et al. . |

FOREIGN PATENT DOCUMENTS 0245662 11/1987 European Pat. Off. .............. 568/75
1083060 3/1989 Japan .

OTHER PUBLICATIONS

Chemical Abstracts, vol. 111, No. 13, Abs. No. 114847x (1989).
Chemical Abstracts, vol. 111, No. 15, Abs. No. 133761f (1989).
Chemical Abstracts, vol. 111, No. 14, Abs. No. 122749g (1989).
Cationic Polymerization . . . Crivello, Adv. in Polym. Sci. 62, p. 3-48.
Aqueous Base Developable Deep . . . , Ito, SPIE vol. 920, pp. 33-41.
Photoinitiated Interfacial . . . Hult et al., Amer. Chem. Soc. p. 1804 1985.
Photoinitiation of Cationic Polymerization . . . Polymer Photochemistry 5 (1984) 1-22.
Applications of Photoinitiatores to the Design of . . . Ito et al. Org. coatings and App. Polym. Sci., Proc. 48, 60 (1983).
Photoinitiated Cationic Polymerization . . . Crivello et al., Jour. of Polym. Sci, vol. 18, 1021-1034 (1980).
Complex Triarylsulfonium Salt Photoinitiators, Crivello et al.
J. of Polymer Sci, vol. 18, 2697-2714 Chemische Berichte 71 (1939) 890.

Primary Examiner—José G. Dees
Assistant Examiner—Porfirio Nazario
Attorney, Agent, or Firm—Keil & Weinkauf

[57] ABSTRACT

Novel sulfonium salts suitable for use as photoinitiators for cationic polymerization and for photoresists have the general formula (I)

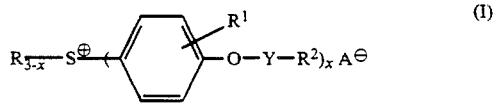

where
X is 1, 2 or 3,
R is a hydrocarbon radical
$R^1$ is hydrogen, alkyl, alkoxy, halogen or nitro,
$R^2$ is a monovalent radical containing more than 6 carbon atoms,
Y is a single bond or a bridge member and
$A^\ominus$ is a non-nucleophilic counterion.

5 Claims, No Drawings

SULFONIUM SALTS AND USE THEREOF

The present invention relates to novel sulfonium salts which in addition to the sulfonium group contain certain functional groups. On irradiation these sulfonium salts form an acid which can then make possible or catalyze secondary reactions. The solubility of the compounds can be varied dramatically through a complete change in the polarity of sulfonium salts as a result of the acid or of a subsequent treatment. The novel sulfonium salts are suitable in particular for use as photoinitiators for cationic polymerization and for use at initiators in photoresists.

Sulfonium salts have long been known in the literature (cf. for example H. M. Pitt, U.S. Pat. No. 2,807,648 (1957); W. Hahn and R. Stroh, U.S. Pat. No. 2,833,827 (1958); G. H. Wiegand and W. E. McEwan, J. Org. Chem., 33 (1968), 2671).

Photoinitiators are almost exclusively sulfonium salts having complex, non-nucleophilic counterions, such as those photoinitiators developed by Crivello for cationic polymerization (cf. for example U.S. Pat. No. 4,058,400 and U.S. Pat. No. 4,058,401). The use of onium salts in cationic polymerization has been reviewed by Crivello in Cationic Polymerisation - Iodonium and Sulfonium Salt Photoinitiators, Advances in Polym. Sci., 62 (1984), 1-48.

The use of onium salts in photoresist materials is described for example in Possibilities for Photoimaging Using Onium Salts, Crivello in Corporate Research and Development, General Electric, Schenectady, N.Y. (1983) and by Ito and Willson in Org. Ctgs. and App. Polym. Sci. Proc. 48 (1983), 60 and U.S. Pat. No. 4,491,628.

Sulfonium salts which form acids as a result of a photochemical reaction have proved useful in cationic polymerization and in photoresist technology. Sulfonium salts were modified in the past essentially only to adapt the solubility (with the aid of inert substituents) and the absorption characteristics to the main emission lines of the light sources used. Apart from the sulfonium salts with acid-labile groups described in DE-A-3,721,740 there are no other sulfonium salts with non-nucleophilic counterions which in addition to the acid-forming sulfonium group contain other functional groups.

The prior art sulfonium salts are very effective initiators for polymerization reactions and effective acid donors in photoresist materials. However, these simple salts are only marginally suitable for use as solubility inhibitors in alkali-soluble matrices. For instance, H. Ito describes in SPIE 920 Advances in Resist Technology and Processing V (1988), 35, that these salts are not capable of effectively inhibiting the solubility of poly(p-hydroxystyrene). DE-A-3,721,740 describes onium salts which in addition to the acid-forming onium group contain acid-labile groups. These salts can be used as solubility inhibitors in alkali-soluble matrices, even for poly(p-hydroxystyrene), but only if fairly high concentrations are used.

It is an object of the present invention to provide significantly better solubility inhibitors and to extend the concept of combining in one and the same molecule acid-forming onium groups and other functional groups which have become redetachable following irradiation or further treatment steps.

We have found that this object is achieved by specific sulfonium salts which in addition to the sulfonium group contain certain functional groups in the same molecule.

The present invention accordingly provides sulfonium salts of the general formula (I)

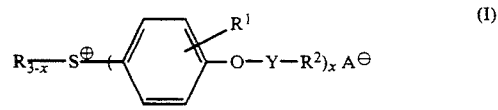

where
x is 1, 2 or 3
R is alkyl, cycloalkyl, aryl, substituted aryl or—if x is 1—a divalent cyclic radical containing $S^\oplus$ as ring member,
$R^1$ is hydrogen, alkyl, alkoxy, halogen or nitro,
$R^2$ is a monovalent aliphatic or aromatic radical of more than 6 carbon atoms which may contain one or more heteroatoms,
Y is a single bond

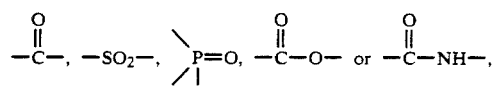

and
$A^\ominus$ is a non-nucleophilic counterion.

In preferred embodiments of the sulfonium salts according to the present invention, $R^2$ in the general formula (I) is an unsubstituted alicyclic radical, an alicyclic radical which is substituted by alkyl, alkoxy, —O—CHO, —O—CO—$CH_3$ or OH, the radical of a photosensitizer molecule, a straight-chain or branched aliphatic hydrocarbon radical of 12 or more carbon atoms, a fluorocarbon radical of 8 or more carbon atoms, or a base-labile radical.

The present invention also provides radiation-sensitive mixtures which contain a sulfonium salt according to the present invention.

The present invention further provides for the use of the sulfonium salts according to the present invention for photoinitiated cationic polymerization and for producing relief patterns or images by using at least one of the sulfonium salts according to the present invention as photoinitiator and solubility inhibitor.

The sulfonium salts according to the present invention are sensitive to UV light, electron beams and X-rays. Suitable counterions are in particular non-nucleophilic anions, for example complex metal halides, such as hexafluoroantimonate, hexafluoroarsenate or tetrafluoroborate, and also trifluoromethanesulfonate, p-toluenesulfonate, perchlorate and fluorosulfonate.

The novel sulfonium salts with non-nucleophilic counterions form on irradiation a strong acid which permits further, secondary reactions, such as the initiation of a cationic polymerization, the initiation of an acid-catalyzed cross-linking reaction or a depolymerization. The alkali-insoluble salts can then be converted into base-soluble phenolic compounds either by the action of the acid formed or by a treatment with a base.

Sulfonium salts according to the present invention are thus for example those which in addition to the sulfonium group contain at least one converted phenolic group in the molecule so that the functional groups are attached in the molecule via ether, ester, carbonate or urethane bonds. Consequently, sulfonium salts according to the present invention are for example those of the general formula (I)

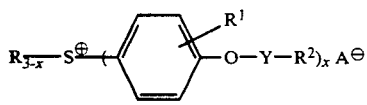

where
x is 1, 2 or 3,
R is alkyl, for example of from 1 to 6, preferably from 1 to 4, carbon atoms, e.g. methyl, ethyl or butyl, cycloalkyl, e.g. cyclohexyl, aryl, e.g. phenyl, substituted aryl, e.g. t-butylphenyl or—if x is 1—a divalent cyclic radical containing $S^\oplus$ as ring member, e.g. a tetrahydrothiophene ring,
$R^1$ is hydrogen, alkyl, for example of from 1 to 6 carbon atoms, e.g. methyl or ethyl, alkoxy, for example of from 1 to 6 carbon atoms, e.g. methoxy or butoxy, halogen, e.g. chlorine or fluorine, or nitro,
$R^2$ is a monovalent aliphatic or aromatic radical of more than 6 carbon atoms which may contain one or more heteroatoms, for example N, S and/or O,
Y is a single bond

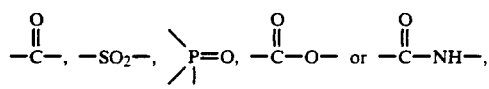

preferably $-\underset{\underset{O}{\|}}{C}-$ or $-\underset{\underset{O}{\|}}{C}-O-$;

and
$A^\ominus$ is a non-nucleophilic counterion, e.g. hexafluoroantimonate, hexafluoroarsenate, tetrafluoroborate, trifluoromethanesulfonate, p-toluenesulfonate, perchlorate or fluorosulfonate.

Examples of sulfonium salts according to the present invention are:

1) sulfonium salts with bulky groups attached to the molecule via acid-labile groups and acting as effective solubility inhibitors, in which case in the general formula (I) Y is

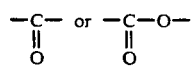

and $R^2$ is an alicyclic or substituted alicyclic radical, i.e. a bulky aliphatic radical, e.g. the 1-adamantine radical, the noradamantane radical or

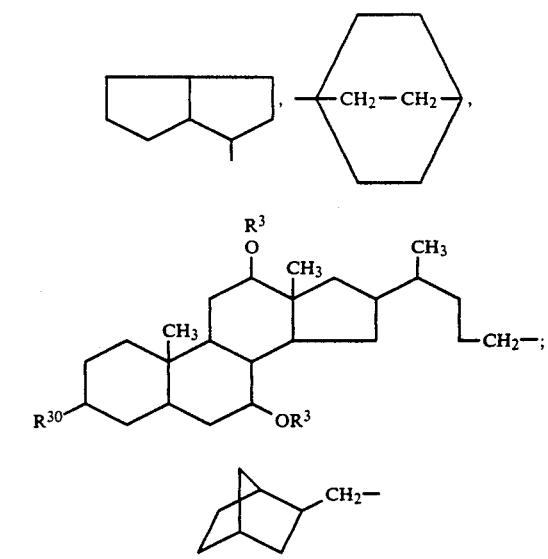

$R^3$ is H, CHO or —CO—CH$_3$;

2) Sylfonium salts containing radicals of photosensitizer molecules, such as

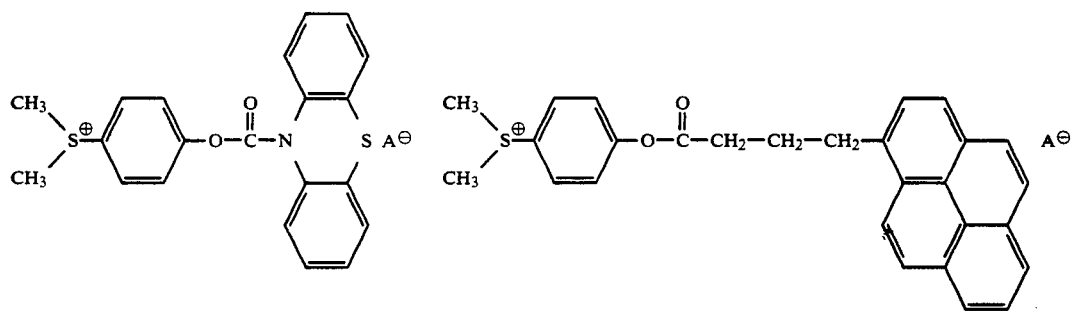

3) Sulfonium salts containing as in the general formula (I) a straight-chain or branched aliphatic hydrocarbon radical of 12 or more, preferably from 12 to 30, carbon atoms or a fluorocarbon radical of 8 or more, preferably from 8 to 18, carbon atoms, i.e. long-chain hydrophobic radicals with a surface-active effect:

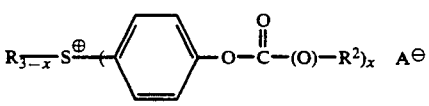

$R^2$ is an aliphatic hydrocarbon radical with $C \geq 8$ or —(CR'$_2$)$_N$—CR'$_3$ or —(CH$_2$)$_n$—CH$_3$ with n=$\geq$11, or an aliphatic fluorocarbon radical with $C \geq 8_2(CR')_3 CR'\underset{n}{} n = \geq 7; R' = H$ and/or F;

4) Sulfonium salts containing base-labile groups, e.g.

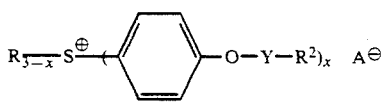

where Y is

and $R^2$ is

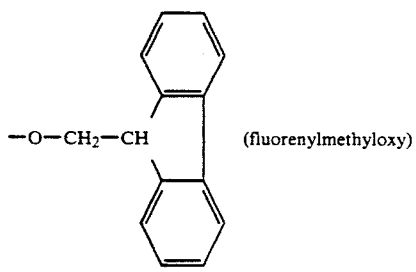 (fluorenylmethyloxy)

Thus, in novel sulfonium salts of the formula

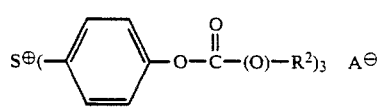

the $R^2$ groups are preferably, as mentioned above, bulky aliphatic radicals, such as the adamantane, noradamantane, cholic acid, norbornylacetic acid or cholesteryl radicals. These radicals are preferably bonded to the molecule via ester or carbonate groups, so that the photoreaction followed by the acid-catalyzed hydrolysis produces alkali-soluble phenolic photoproducts, for example according to the scheme:

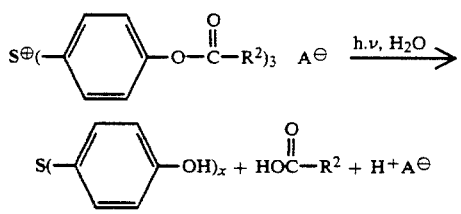

and others.

For some applications, for example if the absorption characteristics of the sulfonium salts are not to be changed but good washability in alkali is required, it is advantageous to have acid-stable protective groups on the sulfonium salt which do not form phenolic, and hence readily soluble, products until treatment with an alkali developer. For this reason the sulfonium salts according to the present invention also include sulfonium salts with base-labile but acid-stable protective groups. Preference is given for example to those sulfonium salts of the formula

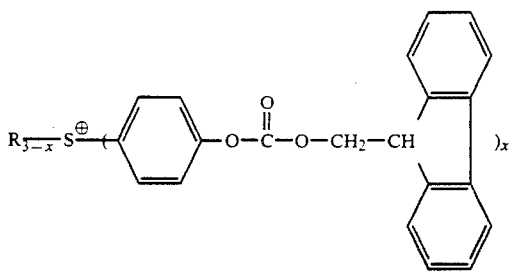

where x is 1 and R is $CH_3$ or x is 3 and R is absent.

Furthermore, for some applications it is advantageous to use compounds which preferentially accumulate at the surface. Examples are the polymerization reactions proposed in Macromolecules 18 (1985), 1804, of monomers at an interface containing the (cationic) initiator. It has been found that those sulfonium salts which contain long aliphatic chains accumulate preferentially at the substrate/air interface on being introduced into polar substrates. According to the present invention, preference is therefore also given to sulfonium salts having hydrocarbon radicals of 12 or more carbon atoms or fluorocarbon radicals $R^2$ of 8 or more carbon atoms, for example

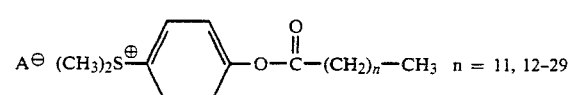

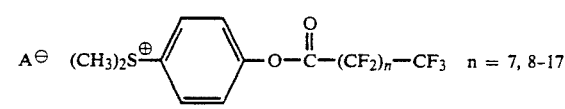

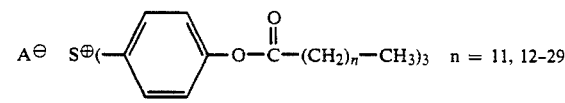

Examples of novel sulfonium salts which contain a sensitizer in the molecule have already been mentioned. It is stated in Polymer Photochemistry 5 (1984), 1–22, that iodonium and sulfonium salts can be sensitized. Of particular suitability are fused aromatics such as perylene, anthracene and phenothiazine. By coupling the sensitizer groups to the moiety to be sensitized it is possible to enhance the effectiveness of sensitization. According to the present invention, preference is given to sulfonium salts of the following formula:

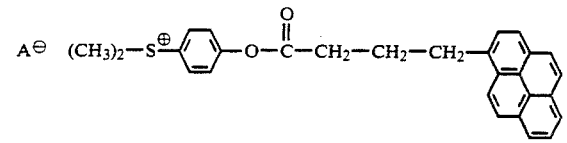

The sulfonium salts according to the present invention can be prepared by the known methods of organic chemistry for the synthesis of esters, carbonates, ethers and urethanes by starting from known sulfonium salts having phenolic groups and reacting them in such a way that the functional groups become bonded to the phenol moiety via esters, carbonates, ethers or urethanes.

The starting compounds which can be used for this purpose are known.

Hydroxyphenyldialkylsulfonium salts which already contain a non-nucleophilic counterion can be prepared for example by the method of J. Polym. Sci., Chem. Ed., 18 (1980), 1021.

Bis(hydroxyphenyl)arylsulfonium salts can be prepared for example by the method of Crivello in J. Polym. Sci., Ed. 18 (1980), 2697, by reacting diaryliodonium salts containing non-nucleophilic counterions with, for example, bis(hydroxyphenyl) sulfides under copper(II) catalysis. These compounds have also already been described in DE-A-3,721,740.

Tris(hydroxyphenyl)sulfonium salts can be prepared for example by the method of U.S. Pat. No. 2,833,827.

There now follow some remarks concerning the synthesis of the novel sulfonium salts having functional groups:

Hydroxyphenylbisalkyl/aryl-, bis(hydroxyphenyl)-aryl- and tris(hydroxyphenyl)-sulfonium salts are advantageously reacted in inert solvents, such as acetonitrile, tetrahydrofuran or ethyl acetate, with acid chlorides, chloroformic esters or isocyanates in the presence or absence of a base. The reaction mixtures are then poured into water and the sulfonium salts can be extracted, for example with acetyl acetate, dried and recrystallized from a suitable solvent.

The sulfonium salts according to the present invention are suitable for use as photoinitiators for the photoinitiated cationic polymerization of, for example, styrene, alkyl vinyl ethers, cyclic ethers and epoxides.

The sulfonium salts according to the present invention are also very advantageously used as photoinitiators and solubility inhibitors in the production of photoresist materials, in which case the polymeric binders used are preferably phenolic resins, such as novolaks, or poly-p-hydroxystyrene.

In the Examples, the parts and percentages are by weight.

EXAMPLE 1

Synthesis of tris[4-(1-adamantanecarbonyloxy)phenyl]-sulfonium trifluoromethanesulfonate Tris(4-hydroxyphenyl)sulfonium chloride is prepared by the method of Chemi. Ber. 72 (1939), 890. 3.47 parts of this salt are dissolved in 20 parts of methanol and mixed with 2.57 parts of silver trifluoromethanesulfonate in 10 parts of methanol. Precipitated silver chloride is filtered off with suction and the solution is evaporated in a rotary evaporator. The crude product thus obtained was used unpurified.

Elemental analysis:

|        | C    | H   | S    | F    | Cl | Ag |
|--------|------|-----|------|------|----|----|
| found: | 49.6 | 3.8 | 13.1 | 11.5 | —  | —  |
| theory:| 49.6 | 3.3 | 13.9 | 12.4 |    |    |

9.2 parts of the tris(hydroxyphenyl)sulfonium trifluoromethanesulfonate thus prepared are dissolved in 150 parts of acetonitrile, and 8 parts of pyridine are added, followed by 11.9 parts of 1-adamantanecarbonyl chloride in 50 parts of acetonitrile, slowly added dropwise. After standing overnight the mixture is filtered, the solvent is evaporated off, and the residue is recrystallized from tetrahydrofuran/naphtha. Yield: 15 parts of the expected product.

IR and H-NMR spectra show that the phenolic band has disappeared and instead an ester band has formed.

Elemental analysis:

|        | C    | H   | S   | F   | Cl  |
|--------|------|-----|-----|-----|-----|
| found: | 64.3 | 6.4 | 6.0 | 5.8 | —   |
| theory:| 65.9 | 6.1 | 6.8 | 6.0 |     |

EXAMPLE 2

Synthesis of tris[4-(fluorenylmethylcarbonyloxy)phenyl]-sulfonium trifluoromethanesulfonate 9.2 parts of the tris(hydroxyphenyl)sulfonium trifluoromethanesulfonate prepared as described in Example 1 are dissolved in 200 parts of acetonitrile. 8 parts of pyridine are added. Thereafter 15.5 parts of fluorenylmethyl chloroformate dissolved in 35 parts of toluene are slowly added dropwise. The mixture is then refluxed for two hours, cooled down, and mixed with 500 parts of 2% strength hydrochloric acid, and extracted with 2000 parts of ethyl acetate a little at a time. After washing the organic solution, the solvent is removed. 16 parts are obtained of the desired product. IR and NMR spectra agree with the expected structure.

The base-labile protective group can be removed quantitatively by treatment with 2N NaOH. The reaction can be monitored by IR and H-NMR spectroscopy.

EXAMPLE 3

Synthesis of dimethyl-4-(pentadecanecarbonyloxy)phenyl-sulfonium hexafluoroarsenate 3.44 parts of dimethyl(hydroxyphenyl)sulfonium hexafluoroarsenate are dissolved in 30 parts of acetonitrile and mixed with 1.01 parts of triethylamine. 2.75 parts of hexadecanoyl. chloride, dissolved in 10 parts of acetonitrile, are then slowly added dropwise at room temperature, the mixture is heated for two hours in a water bath and filtered, and the solvent is drawn off under reduced pressure. The yield of sulfonium salt is 3.5 parts. IR and H-NMR spectra confirm the expected structure.

The preferential accumulation of the sulfonium salts at the surface can be demonstrated by adding 10% of the salt into a matrix of a commercial novolak and spin coating the mixture in a film thickness of 1.5 μm onto a silicon wafer and then using ESCA spectroscopy to determine the concentration of sulfur and arsenic at the surface compared with a similarly prepared sample of unconverted dimethyl(hydroxyphenyl)sulfonium hexafluoroarsenate as salt. It is found that the arsenic and sulfur concentration in the case of the sulfonium salt having a long-chain aliphatic radical is more than twice as high as in the case of the unsubstituted derivative.

EXAMPLE 4

Synthesis of dimethyl-4-(3-(1-pyrenyl)propylcarbonyl)-phenylsulfonium hexafluoroarsenate Commercial 4-(1-pyrenyl)butyric acid is reacted with thionyl chloride to give the carbonyl chloride. 3.06 parts of this chloride are then added to a solution of 3.44 parts of dimethyl(hydroxyphenyl)sulfonium hexafluoroarsenate in 30 parts of acetonitrile and 1.01 parts of triethylamine. After standing overnight and filtering, the solvent is removed. IR and H-NMR spectra confirm the presence of the expected compound. Use as photoinitiator:

A mixture of 30 parts of distilled styrene, 0.5 part of the sulfonium salt prepared as described in Example 4 and 10 parts of tetrachloromethane is irradiated under nitrogen with a mercury lamp (with interference filter, transparent at 365 nm) for 15 minutes. An exothermic polymerization takes place and the reaction solution becomes viscous. Thereafter the reaction solution is diluted and precipitated in methanol.

I claim:

1. A sulfonium salt of the formula (I)

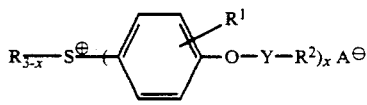

where (1)
x is 1, 2 or 3,
R is alkyl, cycloalkyl, aryl provided x is 2 or 3, substituted aryl or—if x is 1—a divalent cyclic radical containing $S^{\oplus}$ as a ring member,
$R^1$ is hydrogen, alkyl, alkoxy, halogen or nitro,
$R^2$ is a monovalent aliphatic, alicyclic or aromatic radical of more than 6 carbon atoms which may contain one or more heteroatoms,
Y is a single bond,

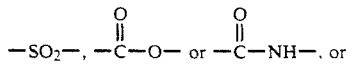

or (2)
x, R, and $R^1$ are as above, $R^2$ is a monovalent alicyclic or aromatic radical of more than 6 carbon atoms which may contain one or more heteroatoms,
Y is a single bond,

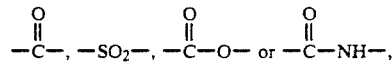

and
$A^{\ominus}$ is a non-nucleophilic counterion.

2. A sulfonium salt as claimed in claim 1, wherein in the formula (I) $R^2$ is an unsubstituted alicyclic radical or an alicyclic radical which is substituted by alkyl, alkoxy, —O—CHO, —O—CO—CH₃ or OH.

3. A sulfonium salt as claimed in claim 1, wherein in the formula(I) $R^2$ is the radical fluorenylmethyloxy.

4. A sulfonium salt as claimed in claim 1, wherein in the formula(I) $R^2$ is a straight-chain or branched aliphatic hydrocarbon radical of 12 or more carbon atoms or a fluorocarbon radical of 8 or more carbon atoms.

5. A sulfonium salt as claimed in claim 1, wherein in the formula (I) $F^2$ is a base-labile radical selected from the group consisting of peryleneyl, anthraceneyl, and phenothiazineyl.

* * * * *

UNITED STATES PATENT AND TRADEMARK OFFICE
CERTIFICATE OF CORRECTION

PATENT NO. : 5,159,088

DATED : October 27, 1992

INVENTOR(S) : Schwalm

It is certified that error appears in the above-identified patent and that said Letters Patent is hereby corrected as shown below:

Claim 5, Column 10, line 29, "$F^2$" should read -- $R^2$ --.

Signed and Sealed this

Fourteenth Day of December, 1993

BRUCE LEHMAN

*Attest:*

*Attesting Officer*   *Commissioner of Patents and Trademarks*